United States Patent [19]

Tsong et al.

[11] 4,271,069
[45] Jun. 2, 1981

[54] BETA-HCG PREPARATION AND METHOD

[75] Inventors: Yun-Yen Tsong, North Caldwell, N.J.; Gursaran P. Talwar, New Delhi, India; Samuel Koide, Dobbs Ferry; Sheldon J. Segal, Hartsdale, both of N.Y.

[73] Assignee: Population Council, Inc., New York, N.Y.

[21] Appl. No.: 946,098

[22] Filed: Sep. 26, 1978

[51] Int. Cl.$^2$ ............... C07C 103/52; H61K 37/00
[52] U.S. Cl. .......................... 260/112.5 R; 424/177
[58] Field of Search ....................... 424/12, 177; 260/112.5 R

[56] References Cited

U.S. PATENT DOCUMENTS 3,992,514  11/1976  Donini .................................. 424/12
4,123,343  10/1978  Krupey et al. ........................ 424/12

OTHER PUBLICATIONS

N. Swaminathan et al., Biochem. and Biophys. Res. Communication, 40, 1970, pp. 422–427.
F. J. Morgan et al., Endocrinology, p. 88, 1045 (1971).

Primary Examiner—Delbert R. Phillips
Attorney, Agent, or Firm—Brumbaugh, Graves, Donohue & Raymond

[57] ABSTRACT

Method of purifying the beta sub-unit of chorionic gondotropin which includes contacting a preparation of the beta sub-unit of chorionic gonadotropin with an insolubilized anti alpha sub-unit of chorionic gondotropin serum and the highly purified beta sub-unit of chorionic gonadotropin obtained by this method.

10 Claims, No Drawings

BETA-HCG PREPARATION AND METHOD

This invention relates to an improved method of purifying the beta sub-unit of CG and to the highly purified beta sub-unit of CG obtained by this method.

The method can be used to purify all mammalian chorionic gonadotropin but for the purpose of illustration human chorionic gonadotropin will be discussed.

Chorionic gonadotropin, hereinafter sometimes referred to as CG is a glycoprotein hormone found in the urine and blood of pregnant mammals, and is considered necessary for the maintenance of pregnancy.

Human chorionic gonadotropin, hereinafter sometimes hCG, has been the subject of intensive investigation. It is composed of two sub-units, which are denominated alpha and beta. The alpha sub-unit of the molecule is identical or nearly identical in chemical structure with the respective alpha sub-units of certain other hormones found in humans, including: thyroid stimulating hormone (TSH), follicle stimulating hormone (FSH) and luteinizing hormone (LH). The beta sub-unit of hCG and the other hormones, in each case, is chemically distinct, and ascribes principally the hormonal specificity.

The beta sub-unit of hCG is a polypeptide of 145 amino acids with 4 out of 6 carbohydrate residues in the C-terminal end. Portions of the beta sub-unit are homologous in amino acid sequence with the beta sub-unit of human LH. The beta sub-unit of hCG prepared by dissociation of highly purified hCG has a fair degree of microheterogeneity. The protein resolves into 8 bands by isoelectric focusing on analytical polyacrylamide gels. This microheterogeneity is observed in commercially available hCG, which is prepared from pregnancy urine. The microheterogeneity may be due to a variable degree of cleavage and/or modifications of molecules during its passage through various tissues.

Much experimentation has been done using hCG and the beta sub-unit of hCG to prepare vaccines to prevent pregnancy. The problem of safely immunizing against pregnancy is discussed in detail in *Contraception*, February, 1976, Vol. 13, No. 2. This search has lead to a realization that it is possible to consider the development of antipregnancy vaccines and thereby antibodies against specific antigenic components of hCG which will cross react in only moderate degree with human LH. Prior to this work, vaccines such as that described by Vernon C. Stevens and C. P. Crystle in Effects of Immunization with Hapten-Coupled hCG on the Human Menstrual Cycle, *Obstetrics and Gynecology*, Vol. 42, No. 4, October, 1973 had been unsuccessful since subjects experienced a depression or obliteration of mid-cycle LH peaks suggesting that the antibodies produced by the vaccine cross react in vivo with endogenous LH. Such cross reaction with the pituitary hormone required for normal function of reproductive organs is undesirable and potentially hazardous.

The cross reaction is thought to be in large measure due to the presence of alpha sub-unit of hCG in the vaccine. Due to the nearly identical structure of the alpha sub-unit of hCG with corresponding portions of the molecule of other endogenous hormones, the antibodies raised by the alpha sub-unit cross react with the hormones having a common alpha sub-unit in this structure. When the beta sub-unit of hCG is used in the preparation of an antipregnancy vaccine, the removal of the last traces of the alpha sub-unit from the preparation as well as undissociated hCG is considered essential.

Dr. G. P. Talwar in *Contraception* supra reported that a vaccine free of cross reaction with endogenous hormones other than hCG can be achieved by subjecting a preparation of a beta sub-unit of hCG to an immunoadsorption purification step and linking the thus-purified beta sub-unit with tetanus toxoid. The Talwar immuno-adsorption purification step removes determinants capable of reacting with high affinity with anti LH sera such as the alpha sub-unit of hCG and the undissociated hCG.

In the method described in *Contraception*, supra, p. 131 the hCG is dissociated with urea. The beta sub-unit is then separated in accordance with known procedures, it is thereafter chemically purified by known means, and then immunochemically purified using a heterologous anti ovine LH immunoadsorbent. It is important in preparing these antipregnancy vaccines that the beta sub-unit of hCG be highly purified both chemically and immunochemically.

In this prior art method, the chemical purification of the beta sub-unit may be effected, for example, by the procedure described in Morgan, F. J. and R. E. Canfield in Endocrinology 88 1045 (1971) and F. J. Morgan and R. E. Canfield, J. L. Vaitukaitis and G. T. Ross, Endocrinoloty 94, pages 1601–1605, (1974). Another suitable method of obtaining a chemically pure preparation of beta sub-unit of hCG is described by Swaiminanthan, N. and Bahl, O.P. in "Dissociation and Recombination of Sub-Units of Human Chorionic Gonadotropin" *Biochemistry, Biophysics Res. Commun.* Vol. 40, page 442, (1970).

After the chemical purification step, the chemically purified beta sub-unit of human chorionic gonadotropin is dissolved in a physiological solvent, such as phosphate buffered saline, and stirred at room temperature for a controlled length of time with an immunoadsorbent such as rabbit antiovine LH. The treatment with the heterologous anti LH immunoadsorbent, under carefully controlled conditions is designed to remove those parts of the preparation which have determinants capable of reacting with high affinity with anti LH sera. The immunoadsorbent used in this process may be selected from any of several heterologous LH anti sera such as rabbit antiovine LH, monkey antiovine LH or antibovine LH. The preparation is thereafter subjected to centrifugation; the precipitate is discarded and the filtrate contains chemically and immunochemically purified beta sub-unit of human chorionic gonadotropin.

This earlier method of purifying the beta sub-unit of hCG has the disadvantage that the antiovine LH sera used contains antibodies which react to some degree with both the alpha and the beta sub-units of hCG. This means that when a beta sub-unit of hCG is treated with antiovine LH sera some of it will react with and thereby remove a portion of the beta sub-unit of hCG as well as the alpha sub-unit and the whole hCG molecule. This results in a lower recovery of purified beta sub-unit of hCG.

It is an object of the present invention to provide an improvement in the method for purifying the beta sub-unit of hCG and specifically to prepare purified beta sub-unit of hCG for use in making an antipregnancy vaccine which produces antibodies with minimal cross reaction with endogenous hormones at physiological levels.

It has now been found that an improved method of purifying the beta sub-unit of chorionic gonadotropin is produced by contacting a preparation thereof with an insolubilized anti hCG alpha sub-unit serum. This is done to remove from the beta sub-unit of CG preparation traces of the alpha sub-unit and undissociated CG without removing beta sub-unit of CG.

In accordance with a preferred embodiment, the improved method for immunochemically purifying the beta sub-unit of CG includes the steps of:

a. Preparing an insolubilized anti hCG alpha sub-unit serum, b. Contacting a preparation of a beta sub-unit of hCG with the insolubilized anti hCG alpha sub-unit serum of step (a) under conditions permitting binding of said insolubilized anti hCG alpha sub-unit serum with contaminants in the preparation of the beta sub-unit, the contaminants including chorionic gonadotropin and an alpha sub-unit thereof, and c. Separating the insolubilized material from the preparation of the beta sub-unit of chorionic gonadotropin.

In accordance with a preferred embodiment of the invention, the step of immunochemically purifying the sub-unit of hCG is accomplished by dissolving the chemically purified beta sub-unit of hCG is a physiological solvent such as phosphate buffered saline, herein sometime referred to as PBS and passing it through a column packed with anti hCG alpha sub-unit serum conjugated at room temperature to a solid support suitable for the separation of high molecular weight proteins.

The column is washed with the phosphate buffered saline and the liquids containing beta sub-unit of hCG are combined, dialyzed against distilled water and lyophilyzed.

This step and all other chromatographic steps of this invention are monitored using a Cary 15 spectrophotometer. HCG and its alpha and beta sub-units absorb at 280 nm and therefore the progress of these materials through the chromatography columns can be monitored by analysing the eluted fractions at that wavelength.

The beta sub-unit of hCG is obtained from crude urinary hCG purchased from Organon, Inc., Oss. Holland. The crude hCG is purified according to known chromatographic methods, for example, the method of Canfield et al. Recent Progr. Horm. Res. 27:124, and dissociated into the alpha and beta sub-units in concentrated urea solutions. The beta sub-unit of hCG is separated and purified by known chromatographic methods for example, that of Morgan and Canfield, *Endocrinology* 88, 1045, 1971, using Sephadex columns.

The anti hCG alpha sub-unit serum is obtained by the immunization of rabbits with the alpha sub-unit of hCG and insolubilized by conjugating it preferably at room temperature to a solid support suitable for the separation of high molecular weight proteins.

Preferably, the solid supports are beads made from material selected from the group consisting of agarose gel, three dimensional polyacrylamide lattice with an interstitial agarose gel and polyacrylamide. Some typical examples of these beads are Sepharose 4B, LKB Ultragel ACA-34, Sephadex and polyacrylamide beads. Sepharose is a bead form agarose gel purchased from Pharmacia Fine Chemicals. LKB Ultragel ACA-34 is composed of beads of a three-dimensional polyacrylamide lattice and an interstitial agarose gel, purchased from Industrie Biologique Francaise and Sephadex is a bead-formed cross-linked dextran gel purchased from Pharmacia Fine Chemicals.

In order to couple the anti hCG alpha sub-unit serum with a solid support, the solid support is activated by pretreatment with the appropriate chemicals and reacted with the anti hCG alpha sub-unit serum. The insolubilized serum is stored under refrigeration.

A chromatography column of suitable size is packed with the insolubilized anti hCG alpha sub-unit serum and a preparation of the chemically purified beta sub-unit of hCG in phosphate buffered saline is passed through the column at room temperature. The column is washed with PBS and the liquids dialysed against glass distilled water until salts were removed as judged by appropriate conductivity measurements. After dialysis, the liquids are lyophilyzed.

In accordance with one of the alternate embodiments of the invention, the immunochemical purification step of the beta sub-unit of hCG is accomplished by dissolving the chemically purified beta sub-unit of human chorionic gonadotropin in a physiological solvent such as PBS and adding equal volumes of anti hCG alpha serum insolubilized by treating the anti hCG alpha serum with 1%-10% preferably 2.5% glutaraldehyde or other aldehydes such as formaldehyde. The mixture of the beta sub-unit of hCG and insolubilized anti hCG alpha serum is held at room temperature with constant stirring for 1 to 2 hours. The suspension is centifuged and the supernatant is removed. The precipitate is washed and all wash liquids are combined with the supernatant, dialyzed against glass distilled water until salts had been removed and lyophilized.

The effectiveness of the method of this invention in removing the alpha sub-unit of hCG and the intact hCG unit is demonstrated by immature rat uterine weight assays of the beta sub-unit of hCG. This assay measures the effect of the purified beta sub-unit of hCG on the uteri of immature rats. The presence of the alpha sub-unit and undissociated hCG in beta sub-unit of hCG preparations injected into immature rats will stimulate a uterine weight gain.

Further objects and advantages of this invention will be more apparent from the ensuing description relating to examples of the preparation of immunochemically pure beta sub-unit of hCG.

EXAMPLE 1

A. Purification of crude hCG

Crude urinary chorionic gonadotropin was purchased from Organon, Inc. Oss. Holland. The potency of the crude material was 2930 units/milligram.

One gram of the crude hCG was dissolved in 20 ml of water, placed in a dialyzing bag of cellulose membrane, and dialyzed against glass-distilled water until salts were removed as judged by conductivity measurements. It was then introduced into a column of 5 cm diameter and 24 cm length containing 30 g of diethylamino-ethyl-cellulose. Development was carried out at 4° C., first with 2500 ml of 0.04 M Tris-phosphate buffer of pH 8.0 and then with 2000 ml of 0.04 M Tris-phosphate buffer of pH 8.0 containing NaCl at a concentration of 0.1 M.

Eluate fractions were monitored by measuring absorption at 280 nm. Fractions that were part of the major peak and showed an optical density of greater than 0.100 were pooled and dialyzed. The dialysis was carried out against glass-distilled water and was monitored by conductivity measurements to determine that the salts have been removed. Dialysis was continued until the conductivity fell to the levels of the distilled water. The dialyzed hCG material was freeze dried.

The freeze-dried hCG material from the diethylaminoethylcellulose column was dissolved in 4 ml of 0.04 M Trisphosphate buffer (pH 8.3) and introduced into a column of 3 cm diameter and containing diethylaminoethyl-Sephadex-A-50 to a depth of 33 cm. Sephadex A-50 is a bead-formed cross-linked dextran gel purchased from Pharmacia Fine Chemicals. Development was conducted with 450 ml each of 0.04 M Tris-phosphate buffer (pH 8.3) and 0.01 M NaCl in 0.04 M Tris-phosphate buffer (pH 8.3) and fractions of 30 ml volume were collected. The two developing solutions were mixed during development so that the development was begun with no NaCl and the concentration of NaCl linearly increased until it reached 0.1 M at the end of the development. Development was then continued with 0.1 M NaCl in 0.04 M Tris-phosphate buffer at pH 8.3 until the bulk of the material absorbing at 280 nm had been eluted. This step might typically require development with an additional 200 ml of the NaCl-Tris-phosphate buffer and will represent a first and a second peak at 280 nm. Fractions comprising the second major peak of absorption at 280 nm were pooled and all other fractions discarded. The pooled fractions containing hCG were dialyzed against glass-distilled water until salts have been removed as judged by conductivity measurements using distilled water as a reference and the fractions containing hCG were freeze-dried.

500 mg of the freeze-dried material from the DEAE-Sephadex A-50 column above were dissolved in 10 ml 0.05 M ammonium acetate at pH 5.0 and placed on a SP-Sephadex C-50 column 5×30 cm. Sephadex C-50 is a bead-formed cross-linked dextran gel purchased from Pharmacia Fine Chemicals. The column was eluted by a continuous gradient formed with 0.05 M ammonium acetate at pH 5 and 0.05 M ammonium acetate containing 0.5 M NaCl. Fractions of 6 ml were collected. The absorbance of each fraction was measured at 280 nm. The protein peak fractions eluted between 0.1–0.25 M NaCl was pooled, dialyzed against glass-distilled water as in previous steps and lyophilized. The average yield of hCG at this step was about 80%. The specific biological activity of the product is about 10,000–12,000 I.U./mg. I.U. is the abbreviation for international units.

B. Dissociation of hCG into Alpha and Beta Sub-Units 400 mg of hCG purified as in A was dissolved in 15 ml of 10 M urea adjusted to pH 4.5 with hydrochloric acid and incubated at 40° C. for one hour. The urea solution of the alpha and beta sub-units was diluted with 30 ml of 0.03 M glycine solution and the pH adjusted to 7.5 with 2 M NaOH.

C. Purification of the Beta Sub-Unit of hCG

Chromatography was carried out in a column of 2.5 cm diameter and packed to a depth of 20 cm with diethylaminoethyl-Sephadex A-25. Sephadex-A-25 is bead-formed cross-linked dextran gel purchased from Pharmacia Fine Chemicals. Before introducing the solution of the hCG sub-units from B, the column was washed with 400 ml of 0.03 M glycine-8 M urea (pH 7.5). Development was begun with the 0.03 M glycine-8 M urea buffer and continued until the first peak, was assayed by absorption at 280 nm, had issued from the column. Development was then begun with 0.2 M glycine-1 M NaCl-8 M urea (pH 7.5) and continued until a second peak at 280 nm had been eluted. Fractions representing the second peak only were pooled, and dialyzed against glass-distilled water until the conductivity had dropped to the level of glass-distilled water and the solution containing the beta sub-unit of hCG was freeze-dried.

D. Immunochemical Purification of Beta Sub-Unit of Human Chorionic Gonadotropin

A column 3×20 cm was packed with 140 ml anti hCG alpha-Sepharose 4B, prepared in the manner described in E infra. The beta sub-unit of hCG as prepared in Steps A–C was dissolved in 10 ml PBS that contained 0.13 M sodium chloride and 0.1 M phosphate, (pH 7.2) and was passed through the column at room temperature. The column was washed with the PBS until the optical density as measured at 280 nm was zero. The fractions containing the beta sub-unit of hCG and the washes were combined and dialyzed against glass-distilled water as in previous steps and lyophilized. The quality of beta hCG sub-unit was determined by rat uterine weight assay. The yield of hCG beta sub-unit was 95% by weight.

E. Preparation of Insoluble Anti-hCG Alpha Sub-Unit Serum by Coupling to a Solid Support 1. Preparation of hCG alpha sub-unit (a) Purification of crude hCG-The hCG was purified as in A.

(b) Dissociation of hCG into alpha and beta sub-units was accomplished as in B.

(c) Separation and Purification of the alpha sub-unit of hCG. Chromatography was carried out in a column of 2.5 cm diameter and packed to a depth of 20 cm with diethylaminoethyl-Sephadex A-25. Sephadex-A-25 is bead-formed cross-linked dextran gel purchased from Pharmacia Fine Chemicals. Before introducing the solution of the hCG sub-units from B, the column was washed with 400 ml of 0.03 M glycine-8 M urea (pH 7.5). Development was begun with the 0.03 M glycine-8 M urea buffer and continued until the first peak, was assayed by absorption at 280 nm, had issued from the column. This fraction containing the alpha sub-unit of hCG was freeze-dried.

100 mg of the freeze-dried hCG alpha sub-unit were dissolved in 2 ml of 50 mM Tris-HCl buffer, containing 0.1 M NaCl at a pH 7.5 and was chromatographed on a 2.6×154 cm column of Sephadex G100, equilibrated with Tris-HCl buffer. The column was then eluted with Tris-HCl buffer and 6 ml fractions were collected and numbered consecutively. Fractions number 74 through 82 were pooled and dialyzed against glass-distilled water as in previous steps and lyophilized. The yield was 34 mg of the alpha sub-unit of hCG.

2. Preparation of the anti hCG alpha sub-unit serum 100 ug of the hCG alpha sub-unit prepared in step E (1) (c) were dissolved in 1 ml of 0.15 M NaCl and emulsified with 1 ml of Freunds complete adjuvant purchased from Difco Co. The 1 ml preparation was administered intradermally to a white New Zealand rabbit weighing from 3–5 kilograms, and the injection was repeated at two week intervals for a total of three 1 ml injections over a four week period. Two weeks after the last 1 ml injection of the alpha sub-unit emulsified with Freunds complete adjuvant, whole blood was collected from the rabbit and the serum was separated. The serum antibody titer was determined by radioimmunoassay.

3. Precipitation of anti hCG alpha sub-unit serum 30 ml anti hCG alpha sub-unit serum as prepared in step 2 above were precipitated with ammonium sulfate at 40% saturation. The precipitate was collected by centrifugation, dissolved in distilled water and dialyzed Nineteen day old Holtzman strain, female rats of 45 to 50 gram weight were used. Five rats were used to test each standard and test solution and ten rats served as controls. Each control rat received a subcutaneous injection 0.5 ml of one percent bovine albumin in 0.9% NaCl solution daily for 3 successive days. Five of the test rats each received a subcutaneous injection of 0.5 ml of the 0.15 IU/ml standard solution daily for three successive days. Five other rats received a subcutaneous injection of 0.5 ml of the 0.3 IU/ml test solution and five others received a subcutaneous injection of 0.5 ml of the 0.6 IU/ml test solution for three successive days. All of the animals were sacrificed 24 hours after the last injection and the uteri removed, trimmed, thoroughly blotted, and weighed to the nearest milligram.

The results in Table 1 below indicate that beta sub-unit of hCG, sample C, prepared in accordance with the method of this invention was found to have a low biological activity of less than 0.5 IU/mg. A standard sample, NIH-CR117, of beta sub-unit of hCG showed an activity of 40.3 and an untreated preparation of beta sub-unit of hCG, sample A showed an activity of 20.0. A beta sub-unit of hCG preparation chemically purified by chromatography on Sephadex, sample B showed an activity of 5.0. These data indicate that only low levels of the intact hCG unit and the alpha sub-unit of hCG were present in the beta sub-unit of hCG prepared according to this invention.

TABLE I

IMMATURE RAT UTERINE WEIGHT ASSAY OF BETA SUB-UNIT OF HCG

| Source | Biological Activity (IU/mg) |
|---|---|
| NIH-CR117 | 40.3 |
| A | 20.0 |
| B | 5.0 |
| C | <0.5 |

We claim:

1. A method of purifying a preparation of a beta sub-unit of chorionic gonadotropin which includes steps of:
   a. preparing an insolubilized anti chorionic gonadotropin alpha sub-unit serum, and
   b. contacting a preparation of the beta sub-unit of chorionic gonadotropin with the insolubilized anti chorionic gonadotropin alpha sub-unit serum of step (a) under conditions permitting binding of said insolubilized alpha sub-unit with contaminants in the preparation of the beta sub-unit, the contaminants including chorionic gonadotropin and an alpha sub-unit thereof, and
   c. separating the insolubilized material from the preparation of the beta sub-unit of chorionic gonadotropin.

2. A method of purifying a preparation of a beta sub-unit of hCG which includes steps of:
   a. forming a mixture of a preparation of a beta sub-unit of hCG with a preparation of anti hCG alpha sub-unit insolubilized with glutaraldehyde, and
   b. holding the mixture under conditions permitting binding of said insolubilized anti hCG alpha sub-unit with contaminants in the preparation of the beta sub-unit, and
   c. separating the preparation of the beta sub-unit of hCG material.

3. The method described in claim 1 wherein the solution is dialyzed against distilled water and lyophilyzed.

4. The method described in claim 2 wherein the solution is dialyzed against distilled water and lyophilyzed.

5. The process defined in claim 2 wherein 2.5% glutaraldehyde is used to insolubilize the anti hCG alpha sub-unit serum.

6. A method of purifying a preparation of a beta sub-unit of hCG which includes steps of:
   a. coupling an anti hCG alpha sub-unit to a solid support suitable for the separation of high molecular weight proteins,
   b. packing a column with the coupled solid support from step (a),
   c. chromatographing a beta sub-unit of hCG through the column prepared in step (b).

7. The process described in claim 6 wherein the chromatographed solution recovered from step (c) is dialyzed against distilled water and lyophilyzed.

8. The process as described in claim 6 wherein, the solid supports are beads made from material selected from the group consisting of agarose gel, three dimensional polyacrylamide lattice with an interstitial agarose gel and polyacrylamide.

9. A preparation of beta sub-unit of CG purified by the process of claim 1.

10. A preparation of beta sub-unit of hCG purified by the process of claim 1.

* * * * *

UNITED STATES PATENT AND TRADEMARK OFFICE
CERTIFICATE OF CORRECTION

PATENT NO. : 4,271,069
DATED : June 2, 1981
INVENTOR(S) : Tsong et al.

It is certified that error appears in the above—identified patent and that said Letters Patent is hereby corrected as shown below:

First page, lines 1 and 2 of ABSTRACT, "gondotropin" should read --gonadotropin--;

First page, line 4 of ABSTRACT, "gondotropin" should read --gonadotropin--;

Col. 2, line 28, "Endocrinoloty" should read --Endocrinology--;

Col. 3, line 25, "is" should read --in--;

Col. 3, line 27, "sometime" should read --sometimes--;

Col. 4, line 14, "were" should read --are--;

Col. 4, line 32, "had" should read --have--;

Col. 5, line 63, "was" should read --as--;

Col. 6, line 43, "was" should read --were--;

Col. 8, last line, before "National" insert --*--.

Signed and Sealed this

Eighth Day of December 1981

[SEAL]

Attest:

GERALD J. MOSSINGHOFF

*Attesting Officer*     *Commissioner of Patents and Trademarks*